US005817820A

United States Patent [19]
Kim et al.

[11] Patent Number: 5,817,820
[45] Date of Patent: Oct. 6, 1998

[54] QUINOLONE DERIVATIVES AND PROCESSES FOR THE PREPARATION THEREOF

[75] Inventors: Wan Joo Kim; Tae Ho Park; Moon Hwan Kim; Jewn Giew Park; Bong Jin Kim, all of Daejeon, Rep. of Korea

[73] Assignee: Korea Research Institute of Chemical Technology, Daejeon, Rep. of Korea

[21] Appl. No.: 277,601

[22] Filed: Jul. 20, 1994

[30] Foreign Application Priority Data

Dec. 9, 1993 [KR] Rep. of Korea .................. 93-27071

[51] Int. Cl.$^6$ .................. C07D 215/56; C07D 471/04
[52] U.S. Cl. .................. 546/156; 544/9; 544/32; 544/66; 544/101; 546/100; 546/113; 546/123
[58] Field of Search .................. 514/300, 312; 546/113, 156, 123, 100; 544/9, 32, 66, 101

[56] References Cited

U.S. PATENT DOCUMENTS

| | | | |
|---|---|---|---|
| 4,146,719 | 3/1979 | Irikura ...................... | 544/363 |
| 4,563,459 | 1/1986 | Grohe et al. .............. | 514/254 |
| 4,954,507 | 9/1990 | Weber et al. ............. | 514/300 |
| 4,965,273 | 10/1990 | Weber et al. ............. | 514/300 |
| 4,990,517 | 2/1991 | Petersen et al. .......... | 514/300 |
| 5,017,581 | 5/1991 | Nishitani et al. ......... | 514/300 |

(List continued on next page.)

FOREIGN PATENT DOCUMENTS

| | | |
|---|---|---|
| 0009425 | 2/1980 | European Pat. Off. . |
| 0047005 | 10/1982 | European Pat. Off. . |
| 0304087 | 2/1989 | European Pat. Off. . |
| 0326916 | 8/1989 | European Pat. Off. . |
| 0366643 | 5/1990 | European Pat. Off. . |
| 0424850 | 5/1991 | European Pat. Off. . |

(List continued on next page.)

OTHER PUBLICATIONS

D. Bouzard et al., "Fluoronaphtyridines as Antibacterial Agents. 4. Synthesis and Structure–Activity Relationships of 5-Substituted-6-fluoro-7-(cycloaklylamino)-1,4-dihydro-4-oxo-1,8-naphthyridine-3-carboxylic Acids", *J. Med. Chem.*, vol. 35, No. 3, pp. 518–525 (1992).

Daniel T. W. Chu, "A Regiospecific Synthesis of 1-Methylamino-6-fluoro-7-(4-methylpiperazin-1-yl)-1,4-dihydro-4-oxoquinoline-3-carboxylic Acid", *J. Heterocyclic Chem.*, vol. 2, pp. 1033–1034 (Jul.–Aug. 1985).

Daniel T. W. Chu et al., "Synthesis and Structure–Activity Relationships of New Arylfluoronaphthyridine Antibacterial Agents", *J. Med. Chem.*, vol. 29, No. 11, pp. 2363–2369 (1986).

John M. Domagala et al., "37-Substituted 5-Amino-1-cyclopropyl-6,8-difluoro-1,4-dihydro-4-oxo-3-quinolinecarboxylic Acids: Synthesis and Biological Activity of a New Class of Quinolone Antibacterials", *J. Med. Chem.*, vol. 31, No. 3, pp. 503–506 (1988).

Hiroshi Egawa et al., "A New Systhesis of 7 H–Pyrido [1,2,3-de] [1,4] benzoaine Derivatives Including and Antibacterial Agent, Ofloxacin", *Chem. Pharm. Bull.*, vol. 34, No. 10, pp. 4098–4102 (1986).

H. Saito et al., "AM–1091", *Drugs of the Future*, vol. 14, No. 10, pp. 931–935 (1989).

*Primary Examiner*—Evelyn Huang
*Attorney, Agent, or Firm*—Baker & Botts, L.L.P.

[57] ABSTRACT

The present invention relates to optical isomers of quinoline compounds of Formula (IA) or Formula (IA'), their pharmaceutically acceptable salts and their intermediates:

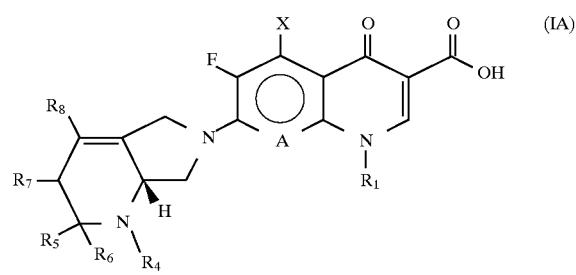

(IA)

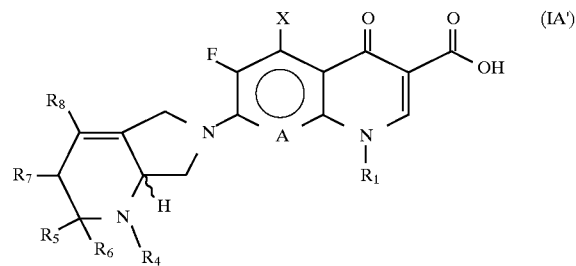

(IA')

In the above formulae, A represent nitrogen or

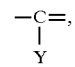

in which Y represents hydrogen, halogen such as fluorine or chlorine, lower alkyl or lower alkoxy such as methoxy, or together with $R_1$ forms —$CH_2CH_2CH_2$—, $CH_2CH_2CH(CH_3)$—, —$OCH_2CH_2$—, —$OCH_2CH(CH_3)$—, —$SCH_2CH_2$— or —$SCH_2CH(CH_3)$—; $R_1$ is as defined above or represents straight chain or cyclic lower alkyl group having 1 to 3 carbon atoms, a straight chain or cyclic lower alkyl group having 1 to 3 carbon atoms which is substituted with a halogen atom, a phenyl group or a phenyl group substituted with one or two halogen atoms, such as ethyl, cyclopropyl or 2,4-difluorophenyl; $R_4$ represents hydrogen, lower alkyl, lower alkoxy, or an amino-protecting group, such as methyl, ethyl or butoxycarbonyl; $R_5$, $R_6$, $R_7$ and $R_8$ may be the same or different and represent independently hydrogen, lower alkyl optionally substituted by amino, hydroxy or halogen, such as methyl or ethyl; and X represents hydrogen, halogen such as fluorine or chlorine, amino or lower alkyl such as methyl.

4 Claims, No Drawings

U.S. PATENT DOCUMENTS

| | | | |
|---|---|---|---|
| 5,059,597 | 10/1991 | Petersen et al. | 514/224.5 |
| 5,091,384 | 2/1992 | Kim et al. | 514/215 |
| 5,140,033 | 8/1992 | Schriewer et al. | 514/312 |
| 5,202,337 | 4/1993 | Petersen et al. | 514/312 |
| 5,498,615 | 3/1996 | Kim | 546/123 |

FOREIGN PATENT DOCUMENTS

| | | |
|---|---|---|
| 0424851 | 5/1991 | European Pat. Off. . |
| 0520277 | 6/1992 | European Pat. Off. . |
| 523512A1 | 7/1992 | European Pat. Off. . |
| 0516861 | 9/1992 | European Pat. Off. . |
| 0549857 | 9/1992 | European Pat. Off. . |
| 550903A1 | 12/1992 | European Pat. Off. . |
| 0588166 | 3/1994 | European Pat. Off. . |
| 3514076 | 10/1985 | Germany . |
| 3632222 | 4/1988 | Germany . |
| 9006307 | 6/1990 | WIPO . |
| 9116310 | 10/1991 | WIPO . |

QUINOLONE DERIVATIVES AND PROCESSES FOR THE PREPARATION THEREOF

The present invention related to novel quinolone compounds, pharmaceutically acceptable salts and optical isomers thereof which possess a broad antibacterial spectrum and exhibit strong antibacterial activity and to processes for preparing these quinolone compounds.

The present invention also relates to optical isomers of diazabicycloalkene derivatives, which may be introduced to the above quinoline compounds, and to processes for preparing the diazabicycloalkene derivatives.

Representatives of the commercially available quinolone antibacterial agents include enoxacin, nonfloxacin, ofloxacin, ciprofloxacin and tosufloxacin. However, it is generally known that these quinolone antibacterials exhibit relatively weak antibacterial activity against Gram-positive bacteria. Furthermore, quinolone-resistant strains have been frequently reported.

Thus, there is still a need for he development of quinolone antibacterials which not only show a broad antibacterial spectrum but also exert strong antibacterial activity against the quinolone-resistant strains.

An object of the present invention is to provide optical isomers of quinoline compounds of Formula (IA) or Formula (IA') and their pharmaceutically acceptable salts.

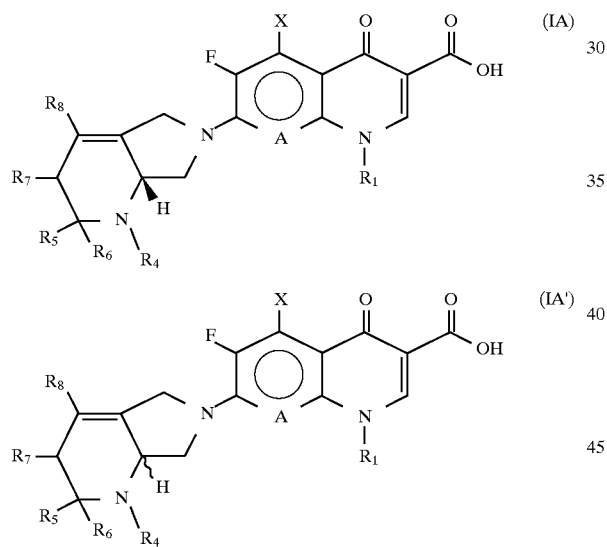

In the above formulae,

A represent nitrogen or

in which Y represents hydrogen, halogen such as fluorine or chlorine, lower alkyl or lower alkoxy such as methoxy, or together with $R_1$ forms —$CH_2CH_2CH_2$—, —$CH_2CH_2CH(CH_3)$—, —$OCH_2CH_2$—, —$OCH_2CH(CH_3)$—, —$SCH_2CH_2$— or —$SCH_2CH(CH_3)$—;

$R_1$ is as defined above or represents a straight chain [or cyclin lower] alkyl group having 1 to 3 carbon atoms, [a straight chain of cyclic lower alkyl group having 1 to 3 carbon atoms] which is optionally substituted with a halogen atom, or a cyclopropyl group which is optionally substituted with a halogen atom, a phenyl group or a phenyl group substituted with one or two halogen atoms, such as ethyl, cyclopropyl or 2,4-diflurorphenyl;

$R_4$ represents hydrogen, lower alkyl, lower alkoxy, or an amino-protecting group, such as methyl, ethyl or butoxycarbonyl;

$R_5$, $R_6$, $R_7$ and $R_8$ may be the same or different and represent independently hydrogen, lower alkyl optionally substituted by amino, hydroxy or halogen, such as methyl or ethyl; and X represents hydrogen, halogen such as fluorine or chlorine, amino or lower alkyl such as methyl.

Lower alkyl is preferably $C_{1-6}$ alkyl, more preferably $C_{1-4}$, such as methyl or ethyl.

Another object of the present invention is to provided optical isomers represented by Formula (Ia) or (Ia'):

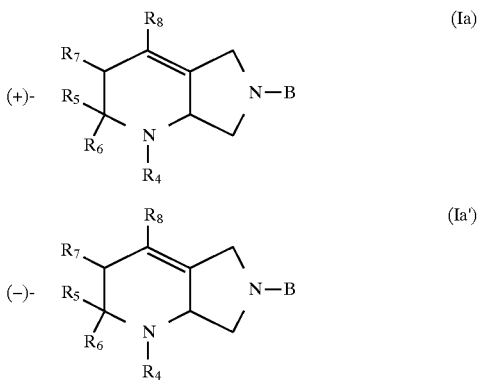

wherein $R_4$, $R_5$, $R_6$, $R_7$ and $R_8$ are the same as defined above, and B is hydrogen, lower alkyl, lower alkoxy, or an amino-protecting group, such as methyl, ethyl or butoxycarbonyl.

Preferred compounds Formula (IA) or (IA') of the present invention which show antibacterial activity and posses a broad antibacterial spectrum are:

1-cyclopropyl-6-fluoro-7-(((+)-2,8-diazabicyclo[4.3.0]non-5-en) -8-yl)-8-methoxy-1,4-dihydro-4-oxo-3-quinoline carboxylic acid;

1-cyclopropyl-6-fluoro-7-(((−)-2,8-diazabicyclo[4.3.0]non-5-en)-8-yl)-8-methoxy-1,4-dihydro-4-oxo-3-quinoline carboxylic acid;

1-cyclopropyl-6-fluoro-7-(((+)-2,8-diazabicyclo[4.3.0]non-5-en)-8-yl)-8-chloro-1,4-dihydro-4-oxo-3-quinoline carboxylic acid;

1-cyclopropyl-5-amino-6,8-difluoro-7-(((+)-2,8-diazabicyclo [4.3.0]non-5-en)-8yl)-1,4-dihydro-4-oxo-3-quinoline carboxylic acid;

9-fluoro-3-(S)-methyl-10-((+)-2,8-diazabicyclo [4.3.0] non-5-en-8-yl)-7-oxo-2,3-dihyro-7H-pyrido [1,2,3-de] -[1,4]-benzoxazin-6-carboxylic acid; and pharmaceutically acceptable salts thereof.

Preferred Compounds of Formula (Ia) or (Ia') of the present invention are (+)-2,8-diazabicyclo[4.3.0]non-5-ene, and (−)-2,8-diazabicyclo[4.3.0]non-5-ene.

Compounds of Formula (Ia) and (Ia') of the present invention may be prepared by the process illustrated below.

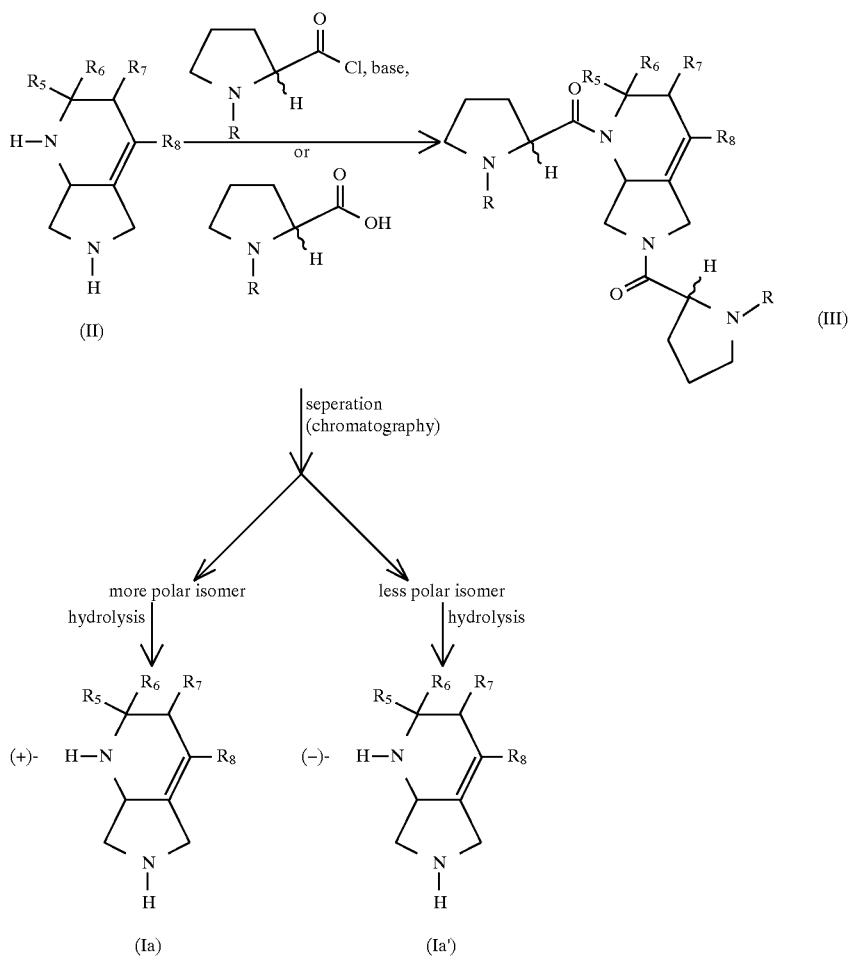

In the above formulae, $R_5$, $R_6$, $R_7$ and $R_8$ are the same as define above, and R represents amine-protecting group such as toluenesulfonyl or t-butoxycarbonyl.

Compound (II) is reacted with N-tosyl-L-prolyl chloride in an organic solvent such as methylene chloride or chloroform or in a mixture of water and the said organic solvents in the presence of an organic base such as triethylamine, 1,8-diazabicyclo[5.4.0]undec-7-ene (DBU) and 1,5-diazabicyclo[4.3.0]non-5-ene (DBN) or an inorganic base such as sodium bicarbonate or sodium carbonate at −20° C. to 30° C. to give Compound (III). Compound (III) may also be prepared by reacting Compound (II) with N-protected L-proline in a solvent such as N,N-dimethylformamide (DMF) dimethyl sulfoxide (DMSO), acetonitrile or chloroform in the presence of an organic or inorganic base such as triethylamine DBU or DBN and dicyclohexyl carbodiimide. Compound (III) is subjected to column chromatography and acid-catalized hydrolysis to obtain Compound (Ia) and Compound (Ia').

Compounds of Formula (IA) or Formula (IA') of the present invention may be prepared, using the compounds of Formula (Ia') above, by the process similar to processes described in U.S. Pat. No. 5,498,615.

The following examples are intended to further explain the present invention, without limiting the scope of the invention.

EXAMPLE 1

Preparation of (+)-2,8-diazabicyclo[4.3.0]non-5-ene dihydrogen chloride

Step (1): Preparation of N,N'-di-(N-tosyl-L-prolyl)-2,8-diazabicyclo[4.3.0]non-5-ene 4.8 g of diazabicyclo[4.3.0]non-5-ene dihydrogen chloride and 13.5 ml of triethylamine were added to 100 ml of chloroform and the reaction mixture was stirred for 5 min. 14.0 g of N-tosyl-L-prolyl chloride in 100 ml of chloroform was added to the reaction mixture under cold temperature (below 0° C.) and the resulting reaction mixture was stirred for 3 hours at room temperature. The reaction mixture was diluted with 200 ml of chloroform, washed with 5% $NaHCO_3$ solution, next with 1N-HCl, and subsequently with NaCl solution, and dried with anhydrous magnesium sulfate. After evaporating the solvent under reduced pressure, the residue was subjected to silica gel column chromatography (ethyl acetate:methanol(v/v)=20:1) to obtain 6.6 g of more polar optical isomer of N,N'-di-(N-tosyl-L-prolyl)-2,8-diazabicyclo[4.3.0]non-5-ene and 5.79 g of less polar optical isomer of N,N'-di-(N-tosyl-L-prolyl)-2,8-diazabicyclo[4.3.0]non-5-ene.

more polar optical isomer: $[\alpha]^{20}_D = -3.4°$ (c=1.0, $CH_3CH_2OH$) $^1H$-NMR($CDCl_3$,δ); 1.7~2.35(9H, m), 2.45 (3H, s), 2.52(3H, s), 3.25~3.60(6H,m),3.52(1H,m),3.29(1H, d),4.13(1H, d),4.33(1H, t),4.40(1H, t), 4.60(2H, m) 5.95(2H, br, s), 7.30(4H, dxd), 7.72(4H, dxd)

less polar optical isomer:$[\alpha]^{20}_D = -23.6.7°$ (c=1.0, $CH_3CH_2OH$) $^1H$-NMR($CDCl_3$, δ); 1.61(1H, m), 1.8~2.2

(9H, m), 2.30~2.42(6H, dxd), 3.0~3.55(6H, m), 3.9~4.35 (3H, m), 4.40~5.0(4H, m), 6.0(1H, m), 7.30(4H, m), 7.75 (4H, m)

Step (2): Preparation of (+)-N,N'-di-t-butoxycarbonyl-2,8-diazabicyclo[4.3.0]non-5-ene To 20 ml of ethanol and 100 ml of 8N-HCl solution was added 7.02 g of the more polar optical isomer of N,N'-di-(N-tosyl-L-prolyl)-2,8-diazabicyclo[4.3.0]non-5-ene and the reaction mixture was stirred for 3 hours under reflux. The resulting reaction mixture was cooled to room temperature and the solvent was evaporated under reduced pressure. To the residue were added 100 ml of methanol and 12.5 ml of triethylamine and the resulting mixture was stirred for 10 min. 9.8 g of di-t-butyldicarbonate was added to the reaction mixture and stirred for 10 hours at room temperature. The reaction solvent was evaporated under reduced pressure. The residue was dissolved in 100 ml of chloroform, washed with water, next with 5% acetic acid and subsequently with NaCl solution, and dried with anhydrous magnesium sulfate. The solovent was evaporated under reduced pressure and the residue was subjected to silica gel column chromatography (ethyl acetate:hexane (v/v)=6:1) to obtain 3.0 g of desired compound (yield: 83%).

$^1$H-NMR(CDCl$_3$,δ); 1.45(9H, s), 1.47(9H, s), 2.15(2H, m), 2.8~2.9(2H, m), 3.9(3H, t), 4.05(1H, t), 4.3~4.4(1H, m), 5.85(1H, br, s)

$[α]^{20}_D$=+179° (c=1.0, MeOH)

Step (3): Preparation of (+)-2,8-diazabicyclo[4.3.0]non-5-ene dihydrogen chloride 3.02 g of (+)-N,N'-di-t-butoxycarbonyl-2,8-diazabicyclo[4.3.0]non-5-ene was dissolved in 18 ml of 8% HCl-methanol solution and stirred for 12 hours at room temperature. The solvent was evaporated under reduced pressure and the 5 ml of ethanol was added to the residue and stirred to give white solid product. The white solid was filtered, washed with mixed solution of ethanol and ethyl ether and dried under reduced pressure to give 1.26 g of desired white solid product (yield; 69%).

$^1$H-NMR(CDCl$_3$,δ); 2.4(2H, m), 3.1~3.3(2H, m), 3.5~3.65(1H, m), 3.8~4.1(3H, m), 4.2~4.4(1H, m), 6.05(1H, br, s)

$[α]^{20}_D$=+1.4° (c=27.2, H$_2$O)

EXAMPLE 2

Preparation of (−)-2,8-diazabicyclo[4.3.0]non-5-ene dihydrogen chloride 7.2 g of the less polar optical isomer of N,N'-di-(N-tosyl-L-propyl)-2,8-diazabicyclo [4.3.0]non-5-ene was treated by the process described in Steps (2) and (3) of Example 1 to give 1.14 g of desired compound.

$[α]^{20}_D$=−1.4° (c=27.2, H$_2$O)

EXAMPLE 3

Preparation of 1-cyclopropyl-6-fluoro-7-(((+)-2,8-diazabicyclo [4.3.0]non-5-en)-8-yl)-8-methoxy-1,4-dihydro-4-oxo-3-quinoline carboxylic acid 195 mg of (+)-2,8-diazabicyclo[4.3.0]non-5-ene dihydrogen chloride, 457 mg of DBU and 295 mg of 1-cyclopropyl-6,7-difluoro-8-methoxy-1,4-dihydro-4-oxo-3-quinoline carboxylic acid were added to 2.5ml of acetonitrile and stirred for 10 hours under reflux. The reaction mixture was cooled to room temperature to result in solid products. The resulting solid product was filtered, washed with 3 ml of acetonitrile and dried to give 312 mg of desired white solid product.

$^1$H-NMR(CDCl$_3$,δ); 1.16(4H, m), 2.11(1H, m), 2.70~4.20(7H, m), 4.02(3H, s), 4.65(1H, d), 5.70(1H, s), 7.84 (1H, d), 8.80(1H, s)

EXAMPLE 4

Preparation of 1-cyclopropryl-6-fluoro-7-(((−)-2,8-diazabicyclo [4.3.0]non-5-en)-8-metnoxy-1,4-dihydro-4-oxo-3-quinoline carboxylic acid 195 mg of (−)-2,8-diazabicyclo[4.3.0]non-5-ene dihydrogen chloride was treated by the process described in Example 3 to give 296 mg of desired compound.

EXAMPLE 5

Preparation of 1-cyclopropyl-6-fluoro-7-(((+)-2,8-diazabicyclo [4.3.0]non-5-en)-8-yl)-8-chloro-1,4-dihydro-4-oxo-3-quinoline carboxylic acid 195 mg of (+)-2,8-diazabicyclo[4.3.0]non-5-ene dihydrogen chloride and 299.5 mg of 1-cyclo-propyl-6,7-difluoro-8-chloro-1,4-dihydro-4-oxo-3-quinoline carboxylic acid were treated by the process described in Example 3 to give 346 mg of desired compound.

$^1$H-NMR(CDCl$_3$,δ); 1.20(4H, m), 2.10(1H, m), 2.30(1H, m), 2.65~4.10(7H, m) 4.93(1H, m), 5.1091H, m), 5.63(1H, ), 7.56(1H, m), 8.61(1H, s)

EXAMPLE 6

Preparation of 1-cyclopropyl-5-amino-6,8-difluoro-7-(((+)-2,8-diazabicyclo [4.3.0]non-5-en)-8-yl)-1,4-dihydro4-oxo-3-quinoline carboxyl acid 195 mg of (+)-2,8-diazabicyclo[4.3.0]non-5-ene dihydrogen chloride and 298 mg of 1-cyclo-propyl-5-amino-6,7,8-trifluoro-1,4-dihydro-4-oxo-3-quinoline carboxylic acid were treated by the process described in Example 3 to give 298 mg of desired compound.

$^1$H-NMR(CDCl$_3$,δ); 1.15(4H, m), 2.1(1H, m), 2.3(1H, m), 2.95(1H, m), 3.2~4.0(6H, m), 4.65(1H, d), 5.75(1H, s), 8.90(1H, s)

EXAMPLE 7

Preparation of 9-fluoro-3-(S)-methyl-10-(((+)-2,8-diazabicyclo [4.3.0]non-5-en)-8-yl)-7-oxo-2,3-dihydro-7H-pyrido [1,2,3-de]-[1,4]-benzoxazin-6-carboxylic acid 200 mg of (+)-2,8-diazabicyclo[4.3.0]non-5-ene dihydrogen chloride and 280 mg of 9,10-difluoro-3-(S)-methyl-7-oxo-2,3-dihydro-7H-pyrido [1,2,3-de]-[1,4]-benzoxazin-6-carboxylic acid were treated by the process described in Example 3 to give 250 mg of desired compound.

$^1$H-NMR(CDCl$_3$,δ); 1.5(3H, d), 2.0(1H, m), 2.85(1H, m), 3.15(1H, m), 3.3~3.6(4H, m), 3.7(1H, m) 3.9(2H, m), 4.2–4.65(4H, m), 5.65(1H, br, s), 7.55(1H, d) 8.5(1H, s)

In vitro antibacterial activity test

The antibacterial activity of the compounds of the present invention was demonstrated in Table 1. The antibacterial activity was determined in accordance with the agar culture medium two-fold dilution method (Hoechst 345) by using a Muller-Hinton agar medium. Hoechst standard strains were used as the test strains. The strains having 10$^7$ CFU/ml were inoculated on the culture medium, and the growth of the strains was observed after incubating them at 37° C. for 18 hours, in which ciprofloxacin was used as a control material.

TABLE 1

| Strain/Substance | Example 3 | Example 4 | Example 5 | Example 6 | Example 7 | ciprofloxacin |
|---|---|---|---|---|---|---|
| Streptococcus pyogenes 308A | 0.195 | 0.781 | 0.195 | 0.098 | 0.781 | 3.125 |
| Streptococcus pyogenes 77A | 0.098 | 0.391 | 0.098 | 0.098 | 0.195 | 0.781 |
| Streptococcus faecium MD8b | 0.098 | 0.195 | 0.098 | 0.049 | 0.195 | 0.781 |
| Staphylococcus aureus SG511 | 0.025 | 0.098 | 0.025 | 0.007 | 0.098 | 0.195 |
| Staphylococcus aureus 285 | 0.025 | 0.098 | 0.025 | 0.013 | 0.195 | 0.391 |
| Staphylococcus aureus 503 | 0.013 | 0.049 | 0.025 | 0.004 | 0.098 | 0.781 |
| Escherichia coli O 78 | 0.004 | 0.025 | 0.007 | <0.002 | 0.025 | <0.002 |
| Escherichia coli DC 0 | 0.195 | 1.563 | 0.195 | 0.098 | 0.391 | 0.195 |
| Escherichia coli DC 2 | 0.025 | 0.098 | 0.025 | 0.025 | 0.098 | 0.098 |
| Escherichia coli TEM | 0.013 | 0.049 | 0.013 | <0.002 | 0.049 | 0.007 |
| Escherichia coli 1507E | 0.013 | 0.098 | 0.013 | 0.004 | 0.049 | 0.007 |
| Pseudomonas aeruginosa 9027 | 1.563 | 3.125 | 0.781 | 0.781 | 0.781 | 0.391 |
| Pseudomonas aeruginosa 1592E | 0.781 | 1.563 | 0.391 | 0.391 | 0.391 | 0.195 |
| Pseudomonas aeruginosa 1771 | 0.781 | 1.563 | 0.391 | 0.391 | 0.781 | 0.195 |
| Pseudomonas aeruginosa 1771M | 0.195 | 0.781 | 0.195 | 0.098 | 0.195 | 0.049 |
| Salmonella typhimurium | 0.007 | 0.049 | 0.007 | 0.004 | 0.025 | 0.007 |
| Klebsiella acrogenes 1082E | <0.002 | 0.007 | <0.002 | 0.007 | 0.013 | <0.002 |
| Klebsiella acrogenes 1552E | 0.025 | 0.098 | 0.013 | 0.007 | 0.098 | 0.013 |
| Enterobacter cloacae P 99 | 0.004 | 0.025 | 0.007 | <0.002 | 0.049 | 0.007 |
| Enterobacter cloacae 1321E | 0.004 | 0.025 | 0.004 | <0.002 | 0.025 | <0.002 |

What is claimed is:

1. A compound of formula (IA) or (IA'):

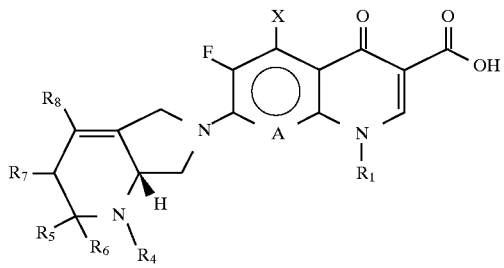
(IA)

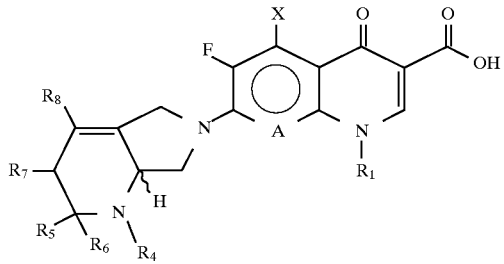
(IA')

wherein, A represents nitrogen or $$-\underset{Y}{\overset{}{C}}=$$

in which Y represents hydrogen, halogen, lower alkyl or lower alkoxy, or together with $R_1$ forms $-CH_2CH_2CH_2-$, $CH_2CH_2CH$ $(CH_3)-$, $OCH_2CH_2-$, $-OCH_2CH(CH_3)-$, $SCH_2CH_2-$ or $SCH_2CH(CH_3)-$;

$R_1$ is as defined above or represents a straight chain alkyl group having 1 to 3 carbon atoms, which is optionally substituted with a halogen atom, a cyclopropyl group which is optionally substituted with a halogen atom atom, a phenyl group or a phenyl group substituted with one or two halogen atoms;

$R_4$ represents hydrogen, lower alkyl, lower alkoxy, organ amino-protecting group;

$R_5$, $R_6$, $R_7$ and $R^8$ are the same or different and represent independently hydrogen, or a lower alkyl optionally substituted by amino, hydroxy or halogen;

X represents hydrogen, halogen, amino or a lower alkyl; or a pharmaceutically acceptable salt thereof.

2. A compound of claim 1, wherein the compound of Formula (IA) or (IA') is as follows:

1-cyclopropyl-6-fluoro-7-(((+)-2,8-diazabicyclo [4.3.0] non-5-en)-8-yl)-8-methoxy-1,4-dihydro-4-oxo-3-quinoline carboxylic acid;

1-cyclopropyl-6-fluoro-7-(((−)-2,8-diazabicyclo [4.3.0] non-5-en)-8-yl)-8-methoxy-1,4-dihydro-4-oxo-3-quinoline carboxylic acid;

1-cyclopropyl-6-fluoro-7(((+)-2,8-diazabicyclo [4.3.0] non-5-en)-8-yl)-8-chloro-1,4-dihydro-4-oxo-3-quinoline carboxylic acid;

1-cyclopropyl-5-amino-6,8-difluroro-7-(((+)-2,8-diazabicyclo [4.3.0]non-5-en)-8-yl)-1,4-dihydro-4-oxo-3-quinoline carboxylic acid;

9-fluoro-3-(S)-methyl-10-((+)-2,8-diazabicyclo [4.3.0] non-5-en-8-yl)-7-oxo-2,3-dihydro-7H-pyrido [1,2,3-de]-[1,4]-benzoxazin-6-carboxylic acid; or a pharmaceutically acceptable salt thereof.

3. A compound of claim 2, wherein the compound of Formula (IA) is 1-cyclopropyl-6-fluoro-7-(((+)-2,8-diazabicyclo [4.3.0]non-5-en)-8-yl)-8-methoxy-1,4-dihydro-4-oxo-3-quinoline carboxylic acid.

4. A compound of claim 2, wherein the compound of Formula (IA') is 1-cyclopropyl-6-fluoro-7-(((−)-2,8-diazabicyclo [4.3.0]non-5-en)-8-yl)-8-methoxy-1,4-dihydro-4-oxo-3-quinoline carboxylic acid.

* * * * *

UNITED STATES PATENT AND TRADEMARK OFFICE
CERTIFICATE OF CORRECTION

Page 1 of 4

PATENT NO. : 5,817,820
DATED : October 6, 1998
INVENTOR(S) : Wan Joo Kim, et al.

It is certified that error appears in the above-identified patent and that said Letters Patent is hereby corrected as shown below:

On the title page:

Item: [54] (Title): "QUINOLONE" should read -- NOVEL QUINOLONE --;

Item: [56] References Cited, OTHER PUBLICATIONS: Under John M. Domagala et al., "37-Substituted" should read -- 7-Substituted --;

Column 1, line 1, "QUINOLONE" should read -- NOVEL QUINOLONE --;

Column 1, line 61, "[or" should be deleted;

Column 1, line 62, "cyclin lower]" should be deleted;

Column 1, line 63, "[a straight chain of cyclic lower alkyl group having 1 to" should be deleted;

Column 2, line 1, "3 carbon atoms]" should be deleted;

Column 2, line 5, "2,4-diflurophenyl;" should read -- 2,4-difluorophenyl; -- ;

Column 2, line 17, "provided" should read -- provide --;

UNITED STATES PATENT AND TRADEMARK OFFICE
CERTIFICATE OF CORRECTION

PATENT NO.  : 5,817,820
DATED       : October 6, 1998
INVENTOR(S) : Wan Joo Kim, et al.

It is certified that error appears in the above-identified patent and that said Letters Patent is hereby corrected as shown below:

Column 2, line 52, "-8yl)-" should read -- -8-yl)- -- ;

Column 3, line 2, "seperation" should read -- separation --

Column 3, line 41, "define" should read -- defined --

Column 3, line 54, "(DMF)" should read -- (DMF), --

Column 3, line 56, "triethylamine DBU" should read -- triethylamine, DBU --;

Column 3, line 62, "Formula (Ia)" should read -- Formula (Ia) or (Ia') --

Column 4, line 45, "diazabicyclo" should read -- 2,8-diazabicyclo --

Column 4, line 66, "23.6.7°" should read -- 236.7° --

Column 6, line 6, "-cyclopropryl-" should read -- -cyclopropyl- --

Column 6, line 7, "-8-metnoxy-" should read -- -8-yl)-8-methoxy- -- ;

UNITED STATES PATENT AND TRADEMARK OFFICE
CERTIFICATE OF CORRECTION

PATENT NO. : 5,817,820
DATED : October 6, 1998
INVENTOR(S) : Wan Joo Kim, et al.

It is certified that error appears in the above-identified patent and that said Letters Patent is hereby corrected as shown below:

Column 6, line 26, "5.1091H, m)," should read -- 5.10 (1H, m), -- ;

Column 6, line 27, " )," should read -- m), -- ; and "7.56 (1H, m)," should read -- 7.56 (1H, d), --;

Column 6, line 33, "dihydro4" should read -- dihydro-4 -- ;

Column 7, Table 1, "Klebsiella acrogenes" (both occurrences) should read -- Klebsiella aerogenes --

Column 7, line 60, "atom" should be deleted;

Column 8, line 24, "organ" should read -- or an -- ;

Column 8, line 26, "$R^8$" should read -- $R_8$ -- ;

Column 8, line 29, "alkyl;" should read -- alkyl, -- ;

UNITED STATES PATENT AND TRADEMARK OFFICE
CERTIFICATE OF CORRECTION

PATENT NO. : 5,817,820
DATED : October 6, 1998
INVENTOR(S) : Kim, et al.

It is certified that error appears in the above-identified patent and that said Letters Patent is hereby corrected as shown below:

Column 8, line 40, "7(((+)" should read -- 7-(((+) -- .

Signed and Sealed this

Twenty-third Day of January, 2001

Attest:

*Attesting Officer*

Q. TODD DICKINSON
*Commissioner of Patents and Trademarks*